(12) United States Patent
Ishikawa

(10) Patent No.: US 8,585,339 B2
(45) Date of Patent: Nov. 19, 2013

(54) SCREW MEMBER

(75) Inventor: Yusuke Ishikawa, Tokyo (JP)

(73) Assignee: GC Corporation, Tokyo (JP)

( * ) Notice: Subject to any disclaimer, the term of this patent is extended or adjusted under 35 U.S.C. 154(b) by 534 days.

(21) Appl. No.: 12/629,286

(22) Filed: Dec. 2, 2009

(65) Prior Publication Data

US 2010/0143071 A1    Jun. 10, 2010

(30) Foreign Application Priority Data

Dec. 2, 2008    (JP) .................................. 2008-307234

(51) Int. Cl.
*F16B 23/00*    (2006.01)

(52) U.S. Cl.
USPC ............................................ 411/408; 81/441

(58) Field of Classification Search
USPC ..................... 411/402, 403, 408, 410; 81/441
See application file for complete search history.

(56) References Cited

U.S. PATENT DOCUMENTS

| | | | | |
|---|---|---|---|---|
| 3,463,209 | A | * | 8/1969 | Podolsky ........................ 81/436 |
| 3,888,144 | A | * | 6/1975 | Parsons ............................ 81/436 |
| 4,269,246 | A | * | 5/1981 | Larson et al. .................... 81/460 |
| 4,503,737 | A | * | 3/1985 | DiGiovanni ..................... 81/436 |
| 5,105,690 | A | * | 4/1992 | Lazzara et al. .................. 81/436 |
| 6,394,806 | B1 | | 5/2002 | Kumar |
| 6,416,324 | B1 | | 7/2002 | Day |
| 6,419,489 | B1 | | 7/2002 | Jörnéus et al. |
| 6,792,838 | B2 | * | 9/2004 | Brooks et al. ................... 81/439 |
| 6,948,408 | B1 | * | 9/2005 | Lee ................................. 81/436 |
| 7,730,812 | B2 | * | 6/2010 | Edland ............................ 81/460 |
| 2007/0037123 | A1 | | 2/2007 | Mansueto et al. |

FOREIGN PATENT DOCUMENTS

JP        2001-500768        1/2001

OTHER PUBLICATIONS

Extended European Search Report dated May 6, 2010 in corresponding European patent application No. 09014955.0-2318.

* cited by examiner

*Primary Examiner* — Flemming Saether
(74) *Attorney, Agent, or Firm* — Oblon, Spivak, McClelland, Maier & Neustadt, L.L.P.

(57) ABSTRACT

For certainly handling a screw member, a screw member 1 includes a male screw 2, and an inner peripheral face of the hole 4 has an engaging recessed part 5 to be engaged with an engaging projected part 11 of a tapered engaging part 10 of a rotary tool 9, and a stepped part 6, said inner peripheral face is parallel or make close to a center axis 7 of the screw member 1 from the head part 3 in a direction of the male screw and from the stepped part 6 in the direction of the male screw, and head part side end edge 8a and an end edge of the stepped part 8b to be engaged with the engaging projected part 11 have an angle of said inner peripheral face being 90±5 degrees with respect to the head part 3 and the stepped part 6.

5 Claims, 2 Drawing Sheets

SCREW MEMBER

BACKGROUND OF THE INVENTION

1. Field of the Invention

The present invention relates to a screw member fastened by a rotary tool (a driver) and, particularly, relates to a screw member properly used for an implant treatment in a dental field.

2. Description of the Conventional Art

A lot of screw members are widely used for an implant treatment in a dental field. More particularly, screw members used in an implant treatment called a two time method will be described as follows. A cover screw is temporarily fastened to an implant fixture, and protects the intraoral side of the implant fixture. The cover screw is used until osseointegration (synostosis) between the implant fixture and a bone is completed after embedding the implant fixture in a primary operation. A healing abutment is temporarily fastened on the intraoral side of an implant exposed by opening a gingiva in a secondary operation, and promotes gingival plasty. A guide pin is used for fastening an impression coping to an implant fixture when collecting an impression for producing a dental prosthesis after the secondary operation. An abutment screw is used to fasten an abutment to an implant fixture. A gold screw is used for fastening a gold cylinder to an abutment, where the gold cylinder becomes to be a base for fixing a dental prosthesis. A soldering screw is used for fastening a gold cylinder to an abutment, where the gold cylinder becomes to be a base for fixing a dental prosthesis when a dental technician produces the dental prosthesis.

Such the screw members are fastened to screw holes of a member, such as an implant fixture, by a rotary tool engaged with an engagement part provided at a head part. However, since this operation is generally carried out in an oral cavity of a patient, the operation for fastening the screw member needs to be carried out in a state that a center axis of the screw hole completely agrees with a center axis of the screw member. Thus, the screw member needs to be moved to a position where the center axis of the screw member completely agrees with the center axis of the screw hole.

Since a screw members cannot be handled directly by hand due to a hygienical reason generally in an implant treatment, the screw member is moved to the screw hole of a member to be fastened in a state of being held with the rotary tool. However, there is a problem that the screw member is dropped in an oral cavity of a patient when moving the screw member.

Further, in many cases, the screw members need to be unfastened and removed after being fastened once. However, the unfastened screw member needs to be easily taken out from the oral cavity in a state of being held with the rotary tool.

In order to solve these problems in the implant treatment, for example, Japanese Translation of PCT Publication No. 2001-500768 discusses a technique to improve ability for making a screw member to be held on a rotary tool. This technique uses wedge effect generated at a head part side end edge of a hole when a top end part of a tapered rotary tool is inserted into a hole formed at a head part of the screw member.

However, when the top end part of the rotary tool is inserted into the hole formed at the head part of the screw member with strong force in order to hold the screw member with the rotary tool, an engagement portion of the head part side end edge of the hole formed at the head part of the screw member may be scratched. When the engagement portion is scratched, the wedge effect is not generated between the screw member and the rotary tool, so that the screw member cannot be moved in a state of being held with the rotary tool. Particularly, as for a screw member which needs to be unfastened and removed after being fastened once, e.g., the cover screw, the top end part of the rotary tool is inserted at least two times into a hole formed at the head part of the screw member with strong force. Thus, the engagement portion of the head part side end edge of the hole formed at the head part of the screw member is scratched, so that a probability that the screw member can not be moved in a state of being held with the rotary tool is high.

SUMMARY OF THE INVENTION

Problem to be Solved by the Invention

The present invention aims to provide to a screw member which can be moved to a screw hole of a member to be fastened in a state of being held with a rotary tool, even when a top end part of the rotary tool is inserted into a hole formed at a head part of the screw member with strong force, and which can be moved after being unfastened in a state of being held with the rotary tool, even when the top end part of the rotary tool is inserted at least two times into the hole formed at the head part of the screw member with strong force in order to unfasten and remove the screw member which is fastened once.

Means for Solving the Problem

Present inventors carried out earnest works to solve the aforementioned problems and, as a result, they found out the followings to complete the present invention. A screw member includes a male screw part, a head part, and a hole formed at the head part. An inner peripheral face of the hole has an engaging recessed part and a stepped part. The engaging recessed part is engaged with an engaging projected part of an engaging part of a rotary tool. The engaging part has a tapered form at an outer peripheral face thereof, is formed at a top end part of a rotary tool, and has the engaging projected part on an outer peripheral face thereof. In a section parallel to a center axis of the screw member, the inner peripheral face of the hole is parallel to the center axis of the screw member or make close to the center axis of the screw member from the head part of the screw member to the direction of the male screw. Further, the inner peripheral face of the hole is parallel or make close to the center axis of the screw member from the stepped part of the screw member to the direction of the male screw. Furthermore, a head part side end edge of the hole and an end edge of the stepped part simultaneously engaged with the engaging projected part of the rotary tool, at the head part side end edge of the hole an angle of the inner peripheral face of the hole and the head part of the screw member is 90±5 degrees, and at the end edge of the stepped part an angle of the inner peripheral face of the hole and the stepped part is 90±5 degrees.

Accordingly, even when the top end part of the rotary tool is inserted into the hole formed at the head part of the screw member with strong force, the engaging projected part on the outer peripheral face of the tapered engaging part, which is the top end part of the rotary tool, is engaged with the head part side end edge of the hole and also engaged with the end edge of the stepped part. The engaging projected part is engaged with all the head part side end edge of the hole and the edge of the stepped part simultaneously. Thus, wedge effect is generated between the screw member and the rotary tool without scratching the engagement portions, so that the screw member can be moved to a member to be fastened in a state of being certainly held with the rotary tool. Further, when the top end part of the rotary tool is inserted at least two times into the hole formed at the head part of the screw member with strong force in order to unfasten and remove the screw member fastened once, it can be prevented that the screw member cannot be moved in a state of being held with the rotary tool because the head part side end edge of the hole and the edge of the stepped part are scratched.

According to an aspect of the present invention, a screw member includes a male screw part, a head part, and a hole formed at the head part, wherein, the inner peripheral face of the hole has engaging recessed part so as to be engaged with an engaging projected part on the outer peripheral face of a tapered engaging part which is a top end part of a rotary tool, and has stepped part, and in a section parallel to a center axis of the screw member, the inner peripheral face of the hole is parallel to the center axis of the screw member or make close to the center axis of the screw member from the head part of the screw member to the direction of the male screw and also is parallel to the center axis of the screw member or make close to the center axis of the screw member from the stepped part of the screw member to the direction of the male screw, and the head part side end edge of the hole and end edge of the stepped part are simultaneously engaged with the engaging projected part of the rotary tool, and the head part side end edge of the hole an angle of the inner peripheral face of the hole and the head part of the screw member is 90±5 degrees and at the end edge of the stepped part an angle of the inner peripheral face of the hole and the stepped part is 90±5 degrees.

According to another aspect of the present invention, the hole formed at the head part of the screw member is configured to have two or more stepped parts and all end edge of the stepped part are simultaneously engaged with the engaging projected part of the rotary tool. In such a configuration, the screw member can be moved to a member to be fastened in a state of more certainly being held with the rotary tool. In addition, when the top end part of the rotary tool is inserted at least two times into the hole formed at the head part of the screw member with strong force in order to unfasten and remove the screw member fastened once, it can be prevented more certainly that the screw member cannot be moved in a state of being held with the rotary tool because the head part side end edge of the hole is scratched. Thus, it is more preferable.

Effect of the Invention

According to a screw member of the present invention, the screw member includes a male screw part, a head part, and a hole formed at the head part, wherein, the inner peripheral face of the hole has an engaging recessed part so as to be engaged with an engaging projected part on an outer peripheral face of a tapered engaging part which is a top end part of a rotary tool, and has a stepped part, and in a section parallel to a center axis of the screw member, the inner peripheral face of the hole is parallel to the center axis of the screw member or make close to the center axis of the screw member from the head part of the screw member to the direction of the male screw, the inner peripheral face of the hole is parallel to the center axis of the screw member or make close to the center axis of the screw member from the stepped part of the screw member to the direction of the male screw, head part side end edge of the hole and end edge of the stepped part are simultaneously engaged with the engaging projected part of the rotary tool, and at the head part side end of the hole an angle of the inner peripheral face of the hole and the head part of the screw member is 90±5 degrees and at the end edge of the stepped part an angle of the inner peripheral face of the hole and the stepped part is 90±5 degrees. Thus, when the top end part of the rotary tool is inserted into the hole formed at the head part of the screw member with strong force, the engaging projected part on the outer peripheral face of the tapered engaging part which is the top end part of the rotary tool is engaged with the head part side end edge of the hole. Further, the engaging projected part is engaged with the end edge of the stepped part. The engaging projected part is engaged with all head part side end edge of the hole and the end edge of the stepped part simultaneously. Thus, wedge effect is generated between the screw member and the rotary tool without scratching the engagement portions, and the screw member can be moved to a member to be fastened in a state of certainly being held with the rotary tool. Further, when the top end part of the rotary tool is inserted at least two times into the hole formed at the head part of the screw member with strong force in order to unfasten and remove the screw member fastened once, it can be prevented that the screw member cannot be moved in a state of being held with the rotary tool because the head part side end edge of the hole and the end edge of the stepped part are scratched.

Further, in another embodiment, the hole includes two or more stepped parts and all end edge of the stepped part are simultaneously engaged with the engaging projected part of the rotary tool. In such a case, the screw member can be moved to a member to be fastened in a state of being more certainly held with the rotary tool. In addition, when the top end part of the rotary tool is inserted at least two times into the hole formed at the head part of the screw member with strong force in order to unfasten and remove the screw member fastened once, it can be prevented more certainly that the screw member cannot be moved in a state of being held with the rotary tool because the head part side end edge of the hole are scratched. Thus, it is more preferable.

DETAILED DESCRIPTION OF PREFERRED EMBODIMENT

Figure 1:
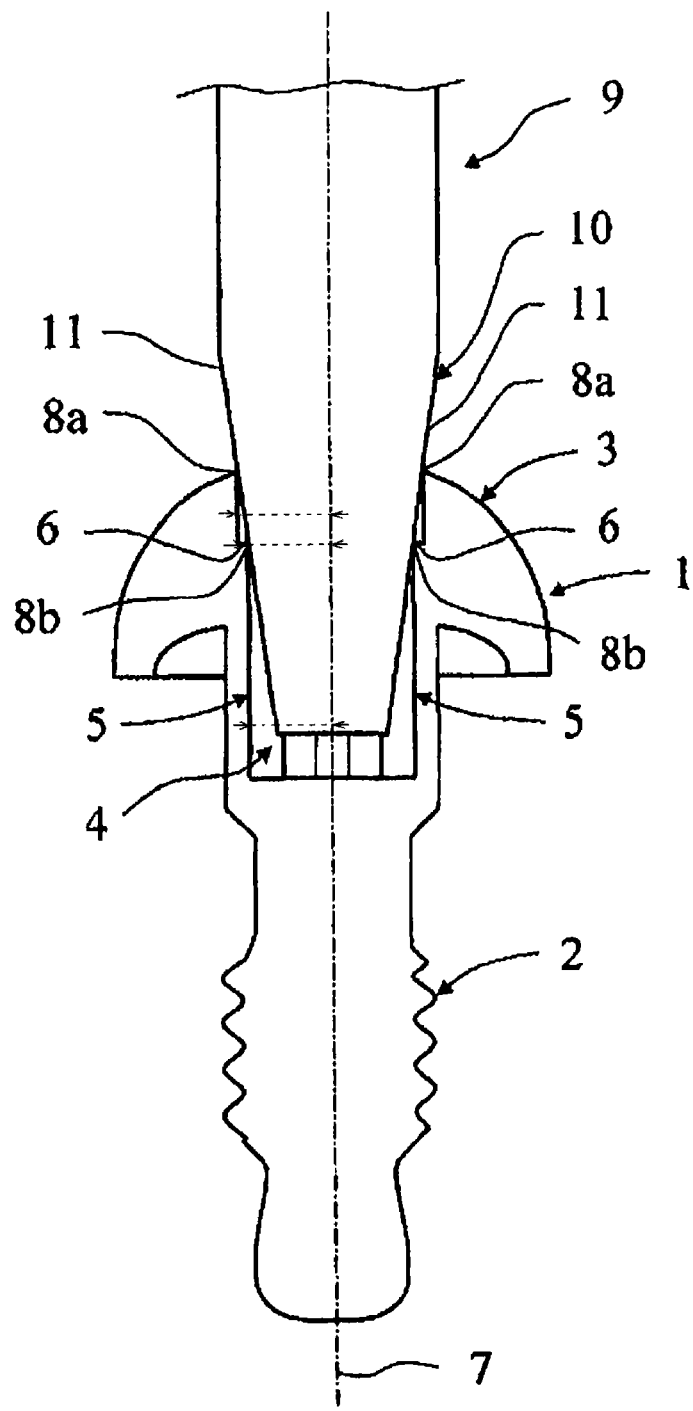
FIG. 1 is a sectional view illustrating a state that a screw member according to the present invention is engaged with a rotary tool at a head part side end of the hole and at an end edge of a stepped part.
Figure 2:
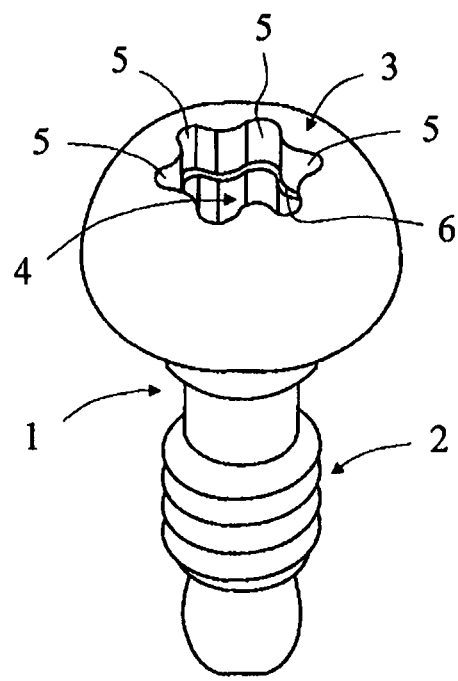
FIG. 2 is a perspective view to illustrate an embodiment of a screw member according to the present invention.
Figure 3:
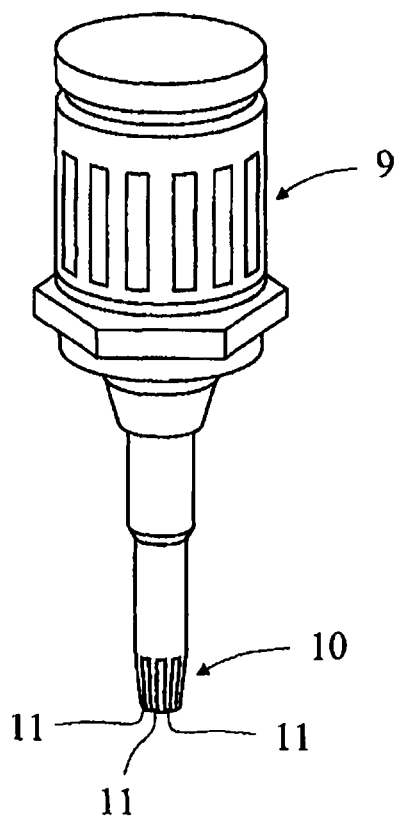
FIG. 3 is a perspective view to illustrate an example of a rotary tool to be engaged with a screw member according to the present invention.

An embodiment of a screw member according to the present invention will be described in detail below with reference to the drawings. FIG. 1 is a sectional view illustrating a state that a screw member according to the present invention is engaged with a rotary tool at a head part side end edge of the hole and at an end edge of a stepped part. FIG. 2 is a perspective view to illustrate an embodiment of a screw member according to the present invention. FIG. 3 is a perspective view to illustrate an example of a rotary tool to be engaged with a screw member according to the present invention.

In these drawings, a screw member 1 according to the present invention includes a male screw part 2 and a head part 3. For example, the screw member 1 is a cover screw, a healing abutment, a guide pin used for fastening an impression coping to an implant fixture, an abutment screw used for fastening an abutment to an implant fixture, a gold screw used for fastening a gold cylinder to be a base for fixing a dental prosthesis to an abutment, or a soldering screw used for fastening a gold cylinder to be a base for fixing a dental prosthesis to an abutment when a dental technician produces the dental prosthesis. These screw members are used when carrying out an implant treatment in a dental field. Such the screw member 1 is generally formed of a material such as titanium or a titanium alloy from the viewpoint of bio-compatibility.

The male screw 2 is screwed into a screw hole of a member to which the screw member 1 is to be fastened, thereby the screw member 1 is fastened to such member. For example, when the screw member 1 is a cover screw, the male screw 2 is screwed into a screw hole formed on the intraoral side of an implant fixture so that the cover screw as the screw member 1 is fastened on the intraoral side of the implant fixture.

The head part 3 includes a hole 4 in which a rotary tool 9 having an engaging projected part 11 on an outer peripheral face of a tapered engaging part 10 at a top end part can be inserted, as illustrated in FIG. 3.

On an inner peripheral face of the hole 4 has an engaging recessed part 5 so as to be engaged with the engaging projected part 11 of the rotary tool 9, and also includes a stepped part 6, as illustrated in FIG. 2. The inner peripheral face of the hole 4 is parallel or slightly closer to a center axis 7 of the screw member 1 toward the male screw 2, in a cross section parallel to the center axis 7 of the screw member 1. Further, the engaging recessed part 5 includes a head part side end edge 8a having an angle of the inner peripheral face of the hole 4 and the head part 3 of the screw member 2 is 90±5 degrees, and an end edge of the stepped part 8b having an angle of the inner peripheral face of the hole 4 and the stepped part 6 is 90±5 degrees. By making the hole 4 to have this configuration, the engaging projected part 11 of the rotary tool 9 is simultaneously engaged with both the head part side end edge 8a and the end edge of the stepped part 8b, and generates wedge effect between the screw member 1 and the rotary tool 9. Thus, when the top end part of the rotary tool 9 is inserted into the hole 4 with strong force, the screw member 1 can be moved to a screw hole of a member to be fastened in a state of being certainly held by the rotary tool 9 without scratching the engagement portions 8a and 8b, and certainly fastened. Further, in the hole 4 having such the configuration, since the engaging projected part 11 of the rotary tool 9 is simultaneously engaged with both the head part side end edge 8a and the end edge of the stepped part 8b of the engaging recess part 5, a shape of the engaging recessed part 5 in the cross section vertical to the center axis 7 of the screw member 1 is not deformed by a torque of the rotary tool 9 which is generated when fastening the screw member 1 to the screw hole of a member to be fastened. Thus, the wedge effect generated between the screw member 1 and the rotary tool 9 is not hindered. Further, if the hole 4 has two or more stepped parts 6, and three or more end edge of the stepped part are engaged with the rotary tool 9, the screw member 1 can be moved to the screw hole of a member to be fastened in a state of more certainly being held by the rotary tool 9. Thus, it is preferable. The aforementioned description is the case that the screw member 1 is fastened with a member to be fastened. However, in a case of the screw member 1 which is necessary to be unfastened and removed after being fastened once, the top end part of the rotary tool 9 is inserted at least two times into the hole 4 formed at the head part 3 of the screw member 1 with strong force. In this case, the engaging projected part 11 of the rotary tool 9 is engaged simultaneously with both the head part side end edge 8a and the end edge of the stepped part 8b and the wedge effect between the screw member 1 and the rotary tool 9 is generated. Thus, even when the top end part of the rotary tool 9 is inserted into the hole 4 with strong force, the unfastened screw member 1 can be moved in a state of being held with the rotary tool 9 without scratching the head part side end edge 8a and the end edge of the stepped part 8b. Furthermore, a shape of the hole 4 in the cross section vertical to the center axis 7 of the screw member 1 is not restricted especially if having the engaging recessed part 5, and a polygon such as a hexagon or an octagon can be used.

What is claimed is:

1. A screw system comprising:
    a rotary tool;
    a male screw;
    a head part; and
    a hole formed at the head part, wherein,
    an inner peripheral face of the hole having an engaging recessed part so as to be engageable with an engaging projected part on an outer peripheral face of a tapered engaging part which is a top end part of the rotary tool, and a stepped part,
    and in a cross section containing a center axis of a screw member, which includes said male screw, head part and hole, the inner peripheral face of the hole is parallel to the center axis of the screw member, or the inner peripheral face of the hole becomes closer to the center axis of the screw member from the head part of the screw member toward the male screw and also is parallel to the center axis of the screw member, or the inner peripheral face of the hole becomes closer to the center axis of the screw member from the stepped part of the screw member toward the male screw,
    and only a head part side end edge of the hole and an end edge of the stepped part simultaneously engage with the engaging projected part of the rotary tool to wedge the engaging projected part,
    and at the head part side end edge of the hole an angle between the inner peripheral face of the hole and the head part of the screw member is 90±5 degrees and at the end edge of the stepped part an angle between the inner peripheral face of the hole and the stepped part is 90±5 degrees.

2. The screw system as claimed in claim 1, wherein the hole has two or more stepped parts and all end edges of the stepped parts are simultaneously engaged with the engaging projected part of the rotary tool.

3. The screw system as claimed in claim 1, wherein the inner peripheral face of the hole includes rounded lobes.

4. The screw system as claimed in claim 1, wherein the engaging recessed part in the cross section is not deformed by a torque from the rotary tool applied to the hole of the screw member.

5. The screw system as claimed in claim 1, wherein the engaging recessed part in the cross section does not contact the rotary tool when the engaging projected part of the rotary tool is inside the hole of the screw member.

* * * * *